United States Patent [19]

Berg et al.

[11] Patent Number: 4,957,595

[45] Date of Patent: * Sep. 18, 1990

[54] SEPARATION OF 3-METHYL-2-BUTANONE FROM FORMIC ACID BY EXTRACTIVE DISTILLATION WITH SULFOLANE

[75] Inventors: Lloyd Berg, 1314 S. 3rd Ave.; George Bentu, both of Bozeman, Mont. 59715

[73] Assignee: Lloyd Berg, Bozeman, Mont.

[ * ] Notice: The portion of the term of this patent subsequent to Aug. 14, 2007 has been disclaimed.

[21] Appl. No.: 432,864

[22] Filed: Nov. 7, 1989

[51] Int. Cl.$^5$ .................. B01D 3/40; C07C 45/83; C07C 51/44

[52] U.S. Cl. .................................. 203/51; 203/56; 203/58; 203/60; 203/61; 203/62; 203/63; 203/64; 203/65; 562/609; 568/410

[58] Field of Search ................ 203/51, 58, 60, 56, 203/61, 62, 63, 64, 65; 568/410; 562/609

[56] References Cited

U.S. PATENT DOCUMENTS

| | | | |
|---|---|---|---|
| 2,570,205 | 10/1951 | Carlson et al. | 203/58 |
| 2,586,929 | 2/1952 | Fleming et al. | 568/440 |
| 3,013,954 | 12/1961 | Pacoud et al. | 203/62 |
| 3,265,592 | 8/1966 | Van Der Weel | 568/410 |
| 3,309,407 | 4/1967 | Carpenter et al. | 568/410 |
| 4,735,690 | 4/1988 | Berg et al. | 203/58 |
| 4,793,901 | 12/1988 | Berg et al. | 203/61 |
| 4,840,707 | 6/1989 | Berg et al. | 203/61 |
| 4,859,285 | 8/1989 | Berg et al. | 203/61 |

*Primary Examiner*—Wilbur Bascomb

[57] ABSTRACT

3-Methyl-2-butanone cannot be separated from formic acid by distillation because of the presence of the maximum boiling azotrope. 3-Methol-2-butanoe can be readily removed from formic acid by extractive distillation using sulfolane. Typical effective agents are: sulfolane and ethylene glycol diacetate; sulfolane, m-toluic acid and anisole.

1 Claim, No Drawings

SEPARATION OF 3-METHYL-2-BUTANONE FROM FORMIC ACID BY EXTRACTIVE DISTILLATION WITH SULFOLANE

FIELD OF THE INVENTION

This invention relates to a method for separating 3-methyl-2-butanone from formic acid using sulfolane as the agent in extractive distillation.

DESCRIPTION OF PRIOR ART

Extractive distillation is the method of separating close boiling compounds or azeotropes by carrying out the distillation in a multi-plate rectification column in the presence of an added liquid or liquid mixture, said liquid(s) having a boiling point higher than the compounds being separated. The extractive agent is introduced near the top of the column and flows downward until it reached the stillpot. Its presence on each plate of the rectification column alters the relative volatility of the close boiling compounds in a direction to make the separation on each plate greater and thus require either fewer plates to effect the same separation or make possible a greater degree of separation with the same number of plates. When the compounds be separated normally form an azeotrope, the proper agents will cause them to boil separately during extractive distillation and thus make possible a separation in a rectification column that cannot be done at all when no agent is present. The extractive agent should boil higher than any of the close boiling liquids being separated and not form minimum azeotropes with them. Usually the extractive agent is introduced a few plates from the top of the column to insure that none of the extractive agent is carried over with the lowest boiling component. This usually requires that the extractive agent boil twenty Celcius degrees or more higher than the lowest boiling component.

At the bottom of a continuous column, the less volatile component of the close boiling mixtures and the extractive agent are continuously removed from the column. The usual methods of separation of these two components are the use of another rectification column, cooling and phase separation or solvent extraction.

3-Methyl-2-butanone, B.P.=95.4° C. and formic acid, B.P.=101° C. form a maximum azeotrope boiling at 102° C. and containing 85% formic acid. Extractive distillation would be an attractive method of separation of 3-methyl-2-butanone from formic acid if agents can be found that (1) will enhance the relative volatility of 3-methyl-2-butanone to formic acid and (2) are easy to recover from the formic acid, that is, form no azeotrope with formic acid and boil sufficiently above formic acid to make separation by rectification possible with only a few theoretical plates. Mixtures forming azeotropes are impossible to separate completely by distillation because the azeotrope is always formed.

Extractive distillation typically requires the addition of an equal amount to twice as much extractive agent as the 3-methyl-2-butanone-formic acid on each plate of the rectification column. The extractive agent should be heated to about the same temperature as the plate on to which it is introduced. Thus extractive distillation imposes an additional heat requirement on the column as well as somewhat larger plates. However this is less than the increase occasioned by the additional agents required if the separation is done by azeotropic distillation. Another consideration in the selection of the extractive distillation agent is its recovery from the bottoms product. The usual method is by rectification in another column. In order to keep the cost of this operation to a minimum, an appreciable boiling point difference between the compound being separated and the extractive agent is desirable. It is desirable that the extractive agent be miscible with formic acid otherwise it will form a two-phase azeotrope with the formic acid in the recovery column and some other method of separation will have to be employed.

Berg, U.S. Pat. No. 4,692,219 separated formic acid from acetic acid by extractive distillation. Extractive distillation was used by Berg, U.S. Pat. No. 4,735,690 to remove water and impurities from formic acid and Berg, U.S. Pat. No. 4,793,901 to break the 2-pentanone-formic acid azeotrope.

OBJECTIVE OF THE INVENTION

The object of this invention is to provide a process or method of extractive distillation that will enhance the relative volatility of 3-methyl-2-butanone from formic acid in their separation in a rectification column. It is a further object of this invention to identify suitable extractive distillation agents that will separate the 3-methyl-2-butanone-formic acid mixtures and make possible the production of pure 3-methyl-2-butanone and formic acid by rectification. It is a further object of this invention to identify organic compounds which in addition to the above constraints, are stable, can be separated from formic acid by rectification with relatively few theoretical plates and can be recycled to the extractive distillation column and reused with little or no decomposition.

SUMMARY OF THE INVENTION

The objects of the invention are provided by a process for separating 3-methyl-2-butanone from formic acid which entails the use of sulfolane admixed with certain oxygen containing organic compounds as the agent in extractive distillation.

DETAILED DESCRIPTION OF THE INVENTION

We have discovered that sulfolane when admixed with other high boiling organic compounds, will effectively negate the azeotrope of 3-methyl-2-butanone and formic acid and permit the separation of pure 3-methyl-2-butanone from formic acid by rectification when employed as the agent in extractive distillation. Table 1 lists the mixtures of sulfolane and organic compounds in the proportions that we have found to be effective. The data in Table 1 was obtained in a vapor-liquid equilibrium still. In each case, the starting material was 25% 3-methyl-2-butanone, 75% formic acid. The ratios are the parts by weight of extractive agent used per part of 3-methyl-2-butanone-formic acid mixture. The relative volatilities are listed for each of the two ratios employed. The compounds which are effective when used in mixtures with sulfolane are adipic acid, azelaic acid, benzoic acid, p-tert. butyl benzoic acid, cinnamic acid, decanoic acid, ethylene glycol diacetate, glycerine triacetate, hexanoic acid, p-hydroxy benzoic acid, itaconic acid, malic acid, neodecanoic acid, m-nitrobenzoic acid, octanoic acid, phenyl acetic acid, sebacic acid, o-toluic acid, m-toluic acid, ethyl phenyl acetate, isobutyl heptyl ketone, acetophenone, cyclohexanone, dipropylene glycol dibenzoate, diethylene glycol dimethyl ether, 2-methoxyethyl ether, glutaric acid, butyl benzoate, ethyl benzoate, methyl benzoate, 3-heptanone, diethylene glycol diethyl ether, isophorone, 4-methyl-2-pentanone, pelargonic acid, benzyl benzoate, salicylic acid, phenyl acetate, diisobutyl ketone, anisole and ethylene glycol phenyl ether.

Table 2 lists several mixtures containing sulfolane which proved to be ineffective.

The two relative volatilities shown in Table 1 correspond to the two different ratios investigated. For example, in Table 1, one half part of sulfolane with one half part of adipic acid with one half part of the 3-methyl-2-butanone-formic acid mixture gives a relative volatility of 3.2; 3/5 parts of sulfolane with 3/5 parts of adipic acid give 3.6. One third parts each of sulfolane and adipic acid give 3.6. One third parts each of sulfolane, m-toluic acid and anisole with one part of the 3-methyl-2-butanone-formic acid mixture gives a relative volatility of 1.5; with 2/5 parts, these three give 1.7. In every example in Table 1, the starting material is the 3-methyl-2-butanone-formic acid azeotrope which possesses a relative volatility of 1.0.

Two of the agents, sulfolane and ethylene glycol diacetate, listed in Table 1 and whose relative volatility had been determined in the vapor-liquid equilibrium still, were then evaluated in a glass perforated plate rectification column possessing 16 theoretical plates and the results listed in Table 3. The data in Table 3 was obtained in the following manner. The charge was 60 grams of 3-methyl-2-butanone and 340 grams of formic acid and after a half hour of operation in the 16 theoretical plate column to establish equilibrium, sulfolane and ethylene glycol diacetate at 85° C. and 12 ml/min. were pumped in. The rectification was continued with sampling of the overhead and bottoms after 30 minutes. The analyses are shown in Table 3 and were: overhead, 98.1% 3-methyl-2-butanone, 1.9% formic acid and the bottoms were 22.1% 3-methyl-2-butanone, 77.9% formic acid which gives a relative volatility of 3-methyl-2-butanone to formic acid of 1.37. After one hour of continuous operation, overhead and bottoms were again sampled and analysed. The overhead was 96.7% 3-methyl-2-butanone, 3.3% formic acid and the bottoms was 15.6% 3-methyl-2-butanone, 84.7% formic acid which is a relative volatility of 1.36. This indicates that the relative volatility has been enhanced from 1.0 and separation accomplished by extractive distillation.

TABLE 1

Effective Extractive Distillation Agents Containing Sulfolane

| Compounds | Ratios | | Relative Volatilities | |
|---|---|---|---|---|
| Sulfolane, Adipic acid | $(\frac{1}{2})^2$ | $(3/5)^2$ | 3.2 | 3.6 |
| Sulfolane, Azelaic acid | " | " | 2.6 | 2.3 |
| Sulfolane, Benzoic acid | " | " | 1.8 | 2.7 |
| Sulfolane, p-tert. Butyl benzoic acid | " | " | 1.9 | 2.4 |
| Sulfolane, Cinnamic acid | " | " | 2.6 | 2.6 |
| Sulfolane, Decanoic acid | " | " | 2.6 | 2.4 |
| Sulfolane, Ethylene glycol diacetate | " | " | 3.2 | 2.8 |
| Sulfolane, Glycerine triacetate | " | " | 2.3 | 2.7 |
| Sulfolane, Hexanoic acid | " | " | 1.9 | 2.5 |

TABLE 1-continued

Effective Extractive Distillation Agents Containing Sulfolane

| Compounds | Ratios | | Relative Volatilities | |
|---|---|---|---|---|
| Sulfolane, p-Hydroxy benzoic acid | " | " | 2.4 | 3.0 |
| Sulfolane, Itaconic acid | " | " | 3.0 | 3.0 |
| Sulfolane, Malic acid | " | " | 2.5 | 2.3 |
| Sulfolane, Neodecanoic acid | " | " | 1.9 | 2.7 |
| Sulfolane, m-Nitrobenzoic acid | " | " | 1.6 | 1.5 |
| Sulfolane, Octanoic acid | " | " | 2.2 | 2.8 |
| Sulfolane, Phenyl acetic acid | " | " | 1.3 | 1.9 |
| Sulfolane, Sebacic acid | " | " | 2.7 | 2.5 |
| Sulfolane, o-Toluic acid | " | " | 1.7 | 1.5 |
| Sulfolane, m-Toluic acid | " | " | 2.4 | 2.0 |
| Sulfolane, Adipic acid, Ethyl phenylacetate | $(\frac{1}{3})^3$ | $(2/5)^3$ | 2.8 | 2.0 |
| Sulfolane, Azelaic acid, Isobutyl heptyl ketone | " | " | 2.0 | 2.1 |
| Sulfolane, Benzoic acid, Acetophenone | " | " | 2.7 | 1.9 |
| Sulfolane, p-tert. Butyl benzoic acid, Dipropylene glycol dibenzoate | " | " | 2.1 | 1.5 |
| Sulfolane, Cinnamic acid, Diethylene glycol dimethyl ether | " | " | 2.8 | 2.1 |
| Sulfolane, Decanoic acid, Cyclohexanone | " | " | 2.3 | 2.1 |
| Sulfolane, Ethylene glycol diacetate, 2-Methoxy-ethyl ether | " | " | 2.8 | 2.8 |
| Sulfolane, Glutaric acid, Ethylene glycol diacetate | " | " | 2.3 | 2.8 |
| Sulfolane, Glycerine triacetate, Butyl benzoate | " | " | 2.3 | 2.0 |
| Sulfolane, Heptanoic acid, Ethyl benzoate | " | " | 1.9 | 1.8 |
| Sulfolane, Hexanoic acid, Methyl benzoate | " | " | 1.7 | 1.7 |
| Sulfolane, p-Hydroxy benzoic acid, 3-Heptanone | " | " | 1.3 | 1.4 |
| Sulfolane, Itaconic acid, Diethylene glycol diethyl ether | " | " | 2.7 | 2.1 |
| Sulfolane, Malic acid, 2-Methoxy ethyl ether | " | " | 3.1 | 3.0 |
| Sulfolane, Neodecanoic acid, Isophorone | " | " | 2.3 | 2.2 |
| Sulfolane, Phenyl acetic acid, 4-Methyl-2-pentanone | " | " | 1.7 | 1.5 |
| Sulfolane, Pelargonic acid, Benzyl benzoate | " | " | 1.6 | 1.7 |
| Sulfolane, Salicylic acid, Phenyl acetate | " | " | 1.5 | 1.5 |
| Sulfolane, Sebacic acid, Diisobutyl ketone | " | " | 2.0 | 2.1 |
| Sulfolane, o-Toluic acid, Ethylene glycol phenyl ether | " | " | 1.6 | 1.7 |
| Sulfolane, m-Toluic acid, Anisole | " | " | 1.5 | 1.7 |

TABLE 2

Extractive Distillation Agents Containing Sulfolane Which Are Ineffective

Sulfolane, Acetyl salicylic acid
Sulfolane, Glutaric acid
Sulfolane, Heptanoic acid
Sulfolane, Pelargonic acid
Sulfolane, Salicylic acid
Sulfolane, Acetyl salicylic acid, Hexyl acetate
Sulfolane, m-Nitrobenzoic acid, Adiponitrile
Sulfolane, Octanoic acid, Butyl benzoate

TABLE 3

Data From Run Made In Rectification Column

| Agent | Column | Time, hrs. | Weight % Ketone | Weight % Formic Acid | Relative Volatility |
|---|---|---|---|---|---|
| 50% Sulfolane, 50% Ethylene glycol diacetate | Overhead | $\frac{1}{2}$ | 98.1 | 1.9 | 1.37 |
| | Bottoms | | 22.1 | 77.9 | |
| 50% Sulfolane, 50% Ethylene glycol | Overhead | 1 | 96.7 | 3.3 | 1.36 |
| | Bottoms | | 15.6 | 84.3 | |

TABLE 3-continued

| | Data From Run Made In Rectification Column | | | | |
|---|---|---|---|---|---|
| Agent | Column | Time, hrs. | Weight % Ketone | Weight % Formic Acid | Relative Volatility |
| diacetate | | | | | |

THE USEFULNESS OF THE INVENTION

The usefulness or utility of this invention can be demonstrated by referring to the data presented in Tables 1 and 3. All of the successful extractive distillation agents show that 3-methyl-2-butanone and formic acid can be separated from each other by means of distillation in a rectification column and that ease of separation as measured by relative volatility is considerable. Without these extractive distillation agents, the relative volatility would be 1.0 and separation by rectification would be impossible. The data also show that the most attractive agents will operate at a boilup rate low enough to make this a useful and efficient method of recovering high purity 3-methyl-2-butanone and formic acid from any mixture of these two including the azeotrope. The stability of the compounds used and the boiling point difference is such that complete recovery and recycle is obtainable by a simple distillation and the amount required for make-up is small.

WORKING EXAMPLES

Example 1

Twelve grams of 3-methyl-2-butanone, 38 grams of formic acid, 25 grams of sulfolane and 25 grams of adipic acid were charged to a vapor-liquid equilibrium still and refluxed for six hours. Analysis indicated a vapor composition of 4.8% 3-methyl-2-butanone, 95.2% formic acid which is a relative volatility of 3.2. Five grams of sulfolane and five grams of adipic acid were added and refluxing continued for another five hours. Analysis indicated a vapor composition of 12.5% 3-methyl-2-butanone, 87.5% formic acid and a liquid composition of 3.8% 3-methyl-2-butanone, 96.8% formic acid which is a relative volatility of 3.6.

Example 2

Fifty grams of the 3-methyl-2-butanone-formic acid mixture, 17 grams of sulfolane, 17 grams of m-toluic acid and 17 grams of anisole were charged to the vapor-liquid equilibrium still and refluxed for six hours. Analysis indicated a vapor composition of 14.3% 3-methyl-2-butanone, 85.7% formic acid and a liquid composition of 10% 3-methyl-2-butanone, 90% formic acid which is a relative volatility of 1.5. Three grams each of sulfolane, m-toluic acid and anisole were added and refluxing continued for another twelve hours. Analysis indicated a vapor composition of 15.9% 3-methyl-2-butanone, 84.1% formic acid and a liquid composition of 10.3% 3-methyl-2-butanone, 89.7% formic acid which is a relative volatility of 1.7.

Example 3

A glass perforated plate rectification column was calibrated with methyl cyclohexane and toluene which possesses a relative volatility of 1.46 and found to have sixteen theoretical plates. A solution comprising 60 grams of 3-methyl-2-butanone and 340 grams of formic acid was placed in the stillpot and heated. When refluxing began, an extractive agent comprising 50% sulfolane and 50% ethylene glycol diacetate was pumped into the column at a rate of 11.5 ml/min. The temperature of the extractive agent as it entered the column was 85° C. After establishing the feed rate of the extractive agent, the heat input to the 3-methyl-2-butanone and formic acid in the stillpot was adjusted to give a total reflux rate of 42 ml/min. After 30 minutes of operation, the overhead and bottoms samples of approximately two ml. were collected and analysed by gas chromatography. The overhead analysis was 98.1% 3-methyl-2-butanone and 1.3% formic acid. The bottoms analysis was 22.1% 3-methyl-2-butanone and 77.9% formic acid. Using these compositions in the Fenske equation, with the number of theoretical plates in the column being 16, gave an average relative volatility of 1.37 for each theoretical plate. After one hour of continuous operation, the overhead analysis was 96.7% 3-methyl-2-butanone, 3.3% formic acid, the bottoms analysis was 15.6% 3-methyl-2-butanone and 85.3% formic acid which is a relative volatility of 1.36. These data are presented in Table 3.

We claim:

1. A method for recovering 3-methyl-2-butanone from a mixture consisting essentially of 3-methyl-2-butanone and formic acid which comprises distilling the mixture consisting essentially of 3-methyl-2-butanone and formic acid in a rectification column in the presence of about one part of an extractive agent per part of 3-methyl-2-butanone-formic acid mixture, recovering 3-methyl-2-butanone as overhead product and obtaining the extractive agent and the formic acid from the stillpot, wherein said extractive agent comprises sulfolane and at least one material selected from the group consisting of adipic acid, azelaic acid, benzoic acid, cinnamic acid, p-tert. butyl benzoic acid, decanoic acid, ethylene glycol diacetate, glycerine triacetate, hexanoic acid, p-hydroxy benzoic acid, itaconic acid, malic acid, neodecanoic acid, m-nitrobenzoic acid, octanoic acid, isobutyl heptyl ketone, cyclohexanone, dipropylene glycol dibenzoate, diethylene glycol dimethyl ether, 2-methoxyethyl ether, glutaric acid, butyl benzoate, ethyl benzoate, methyl benzoate, 3-heptanone, diethylene glycol diethyl ether, isophorone, 4-methyl-2-pentanone, pelargonic acid, benzyl benzoate, phenyl acetate, anisole and ethylene glycol phenyl ether.

* * * * *